US006953675B2

(12) United States Patent
Leung et al.

(10) Patent No.: US 6,953,675 B2
(45) Date of Patent: Oct. 11, 2005

(54) LANDSCAPED ANTIBODIES AND ANTIBODY FRAGMENTS FOR CLINICAL USE

(75) Inventors: Shui-on Leung, Madison, NJ (US); William J. McBride, Summit, NJ (US); Zhengxing Qu, Warren, NJ (US); Hans Hansen, Mystic Island, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 09/185,607

(22) Filed: Nov. 4, 1998

(65) Prior Publication Data

US 2002/0193572 A1 Dec. 19, 2002

Related U.S. Application Data

(60) Provisional application No. 60/064,386, filed on Nov. 6, 1997.

(51) Int. Cl.$^7$ ................................................ C12P 21/04
(52) U.S. Cl. ..................... 435/69.6; 530/387.1; 435/325
(58) Field of Search ................................ 435/69.6, 325; 530/387.3, 391.8, 391.5, 300; 536/320.1, 23.53

(56) References Cited

U.S. PATENT DOCUMENTS

| | | | |
|---|---|---|---|
| 5,057,313 A | * | 10/1991 | Shih et al. |
| 5,120,526 A | | 6/1992 | Fritzberg et al. |
| 5,175,343 A | | 12/1992 | Fritzberg et al. |
| 5,242,679 A | | 9/1993 | Fritzberg et al. |
| 5,443,953 A | * | 8/1995 | Hansen et al. |

FOREIGN PATENT DOCUMENTS

| | | |
|---|---|---|
| WO | WO 90 03401 A | 4/1990 |
| WO | WO 95 15769 A | 6/1994 |
| WO | WO 97 34632 A | 9/1997 |

OTHER PUBLICATIONS

Li, et al., bioconjugate chem. 4:275–283, 1993.*
Dalente, Trends in biotechnology vol. 3, 1985.*
Olden et al., Biochimica et Biophysica Acta. 650:209–232, 1982.*
Wright et al., Springer Semin Immunopathol 15:259–273, 1993.*
Paul., Fundamental Immunology , Raven Press NY, Chapter 8, p. 242, 1993.*
L.K. Mahal et al., "Engineering Chemical Reactivity on Cell Surfaces Through Oligosaccharide Biosynthesis," *Science*, vol. 276, pp1125–1128, May 16, 1977.
Z. Qu et al., "Structure Determination of N–linked Oligosaccharides Engineered at the CH1 Domain of Humanized LL2," *Glycobiology*, vol. 7, No. 6, pp 803–809, Sep. 6, 1997.
S. Leung et al., "Effect of VK Framework–1 Glycosylation on the Binding Affinity of Lymphoma–Specific Murine and Chimeric LL2 Antibodies and Its Potential use as a Novel Conjugation Site," *Intl. J. of Cancer*, vol. 60, No. 12, pp 534–538, Feb. 8, 1995.
S. Leung et al., Engineering A Unique Glycosylation Site for Site–Specific Conjugation of Haptens to Antibody Fragements, *Journal of Immunology*, vol. 154, No. 6, pp 5919–5926, Mar. 15, 1995.
Z. Qu et al., "Carbohydrates Engineered at Antibody Constant Domains Can Be Used for Site–Specific Conjugation of Drugs and Chelates," *Journal of Immunological Methods*, vol. 213, No. 2, pp 131–144, Apr. 15, 1998.
Brennan; "Carbohydrate–Based Drug Delivery"; C&EN; May 5, 1997; pp. 50–54.

* cited by examiner

*Primary Examiner*—Larry R. Helms
(74) *Attorney, Agent, or Firm*—Heller Ehrman LLP

(57) ABSTRACT

A method of making a glycosylated antibody or antibody fragment having a reactive ketone group on the glycosylated site is provided. The method comprises expressing a cell transfected with a vector encoding an antibody having one or more glycosylation sites in a culture medium comprising a ketone derivative of a saccharide or saccharide precursor and, in the case of an antibody fragment, fragmenting the resulting antibody into an antigen-binding antibody fragment. Methods of making immunoconjugates comprising the glycosylated antibodies or antibody fragments also are provided, wherein the antibody or antibody fragment is reacted with an agent comprising a ketone-reactive group. Glycosylated antibodies and antibody fragments having a reactive ketone group on the glycosylated site, immunoconjugates comprising such antibodies and antibody fragments and in vivo targeting methods using such antibodies, antibody fragments and immunoconjugates also are provided.

7 Claims, No Drawings

SEQUENCE LISTING

<160> NUMBER OF SEQ ID NOS: 14

<210> SEQ ID NO 1
<211> LENGTH: 49
<212> TYPE: PRT
<213> ORGANISM: Homo sapiens

<400> SEQUENCE: 1

Pro Glu Pro Val Thr Val Ser Trp Asn Ser Gly Ala Leu Thr Ser Gly
  1               5                  10                  15

Val His Thr Phe Pro Ala Val Leu Gln Ser Ser Gly Leu Tyr Ser Leu
             20                  25                  30

Ser Ser Val Val Thr Val Pro Ser Ser Ser Leu Gly Thr Gln Thr Tyr
         35                  40                  45

Ile

<210> SEQ ID NO 2
<211> LENGTH: 49
<212> TYPE: PRT
<213> ORGANISM: Homo sapiens

<400> SEQUENCE: 2

Pro Glu Pro Val Thr Val Ser Trp Asn Ser Ser Ala Leu Thr Ser Gly
  1               5                  10                  15

Val His Thr Phe Pro Ala Val Leu Gln Ser Ser Gly Leu Tyr Ser Leu
             20                  25                  30

Ser Ser Val Val Thr Val Pro Ser Ser Ser Leu Gly Thr Gln Thr Tyr
         35                  40                  45

Ile

<210> SEQ ID NO 3
<211> LENGTH: 49
<212> TYPE: PRT
<213> ORGANISM: Homo sapiens

<400> SEQUENCE: 3

Pro Glu Pro Val Thr Val Ser Trp Asn Ser Gly Ala Leu Thr Ser Gly
  1               5                  10                  15

Val His Thr Phe Pro Ala Val Leu Asn Ser Ser Gly Leu Tyr Ser Leu
             20                  25                  30

Ser Ser Val Val Thr Val Pro Ser Ser Ser Leu Gly Thr Gln Thr Tyr
         35                  40                  45

Ile

<210> SEQ ID NO 4
<211> LENGTH: 49
<212> TYPE: PRT
<213> ORGANISM: Homo sapiens

<400> SEQUENCE: 4

Pro Glu Pro Val Thr Val Ser Trp Asn Ser Gly Ala Leu Thr Ser Gly
  1               5                  10                  15

Val His Thr Phe Pro Ala Val Leu Gln Ser Ser Gly Leu Tyr Ser Asn
             20                  25                  30

Ser Ser Val Val Thr Val Pro Ser Ser Ser Leu Gly Thr Gln Thr Tyr
         35                  40                  45

Ile

```
<210> SEQ ID NO 5
<211> LENGTH: 49
<212> TYPE: PRT
<213> ORGANISM: Homo sapiens

<400> SEQUENCE: 5

Pro Glu Pro Val Thr Val Ser Trp Asn Ser Gly Ala Leu Thr Ser Gly
 1               5                  10                  15

Val His Thr Phe Pro Ala Val Leu Gln Ser Ser Gly Leu Tyr Ser Leu
            20                  25                  30

Ser Ser Val Val Thr Val Pro Asn Ser Ser Leu Gly Thr Gln Thr Tyr
        35                  40                  45

Ile

<210> SEQ ID NO 6
<211> LENGTH: 49
<212> TYPE: PRT
<213> ORGANISM: Homo sapiens

<400> SEQUENCE: 6

Pro Glu Pro Val Thr Val Ser Trp Asn Ser Gly Ala Leu Thr Ser Gly
 1               5                  10                  15

Val His Thr Phe Pro Ala Val Leu Gln Ser Ser Gly Leu Tyr Ser Leu
            20                  25                  30

Ser Ser Val Val Thr Val Pro Ser Ser Asn Gly Thr Gln Thr Tyr
        35                  40                  45

Ile

<210> SEQ ID NO 7
<211> LENGTH: 53
<212> TYPE: PRT
<213> ORGANISM: Homo sapiens

<400> SEQUENCE: 7

Pro Arg Glu Ala Lys Val Gln Trp Lys Val Asp Asn Ala Leu Gln Ser
 1               5                  10                  15

Gly Asn Ser Gln Glu Ser Val Thr Glu Gln Asp Ser Lys Asp Ser Thr
            20                  25                  30

Tyr Ser Leu Ser Ser Thr Leu Thr Leu Ser Lys Ala Asp Tyr Glu Lys
        35                  40                  45

His Lys Val Tyr Ala
    50

<210> SEQ ID NO 8
<211> LENGTH: 53
<212> TYPE: PRT
<213> ORGANISM: Homo sapiens

<400> SEQUENCE: 8

Pro Arg Glu Ala Lys Val Gln Trp Lys Val Asp Asn Ala Leu Gln Ser
 1               5                  10                  15

Gly Asn Ser Asn Glu Ser Val Thr Glu Gln Asp Ser Lys Asp Ser Thr
            20                  25                  30

Tyr Ser Leu Ser Ser Thr Leu Thr Leu Ser Lys Ala Asp Tyr Glu Lys
        35                  40                  45

His Lys Val Tyr Ala
    50
```

```
<210> SEQ ID NO 9
<211> LENGTH: 53
<212> TYPE: PRT
<213> ORGANISM: Homo sapiens

<400> SEQUENCE: 9

Pro Arg Glu Ala Lys Val Gln Trp Lys Val Asp Asn Ala Leu Gln Ser
 1               5                  10                  15

Gly Asn Ser Gln Glu Ser Val Thr Glu Gln Asp Ser Lys Asp Ser Thr
                20                  25                  30

Tyr Asn Leu Ser Ser Thr Leu Thr Leu Ser Lys Ala Asp Tyr Glu Lys
            35                  40                  45

His Lys Val Tyr Ala
        50

<210> SEQ ID NO 10
<211> LENGTH: 53
<212> TYPE: PRT
<213> ORGANISM: Homo sapiens

<400> SEQUENCE: 10

Pro Arg Glu Ala Lys Val Gln Trp Lys Val Asp Asn Ala Ser Gln Ser
 1               5                  10                  15

Gly Asn Ser Gln Glu Ser Val Thr Glu Gln Asp Ser Lys Asp Ser Thr
                20                  25                  30

Tyr Ser Leu Ser Ser Thr Leu Thr Leu Ser Lys Ala Asp Tyr Glu Lys
            35                  40                  45

His Lys Val Tyr Ala
        50

<210> SEQ ID NO 11
<211> LENGTH: 53
<212> TYPE: PRT
<213> ORGANISM: Homo sapiens

<400> SEQUENCE: 11

Pro Arg Glu Ala Lys Val Gln Trp Lys Val Asp Asn Ala Leu Gln Ser
 1               5                  10                  15

Gly Asn Ser Gln Glu Ser Val Thr Glu Gln Asp Ser Lys Asp Ser Thr
                20                  25                  30

Tyr Ser Leu Ser Ser Thr Leu Asn Leu Ser Lys Ala Asp Tyr Glu Lys
            35                  40                  45

His Lys Val Tyr Ala
        50

<210> SEQ ID NO 12
<211> LENGTH: 53
<212> TYPE: PRT
<213> ORGANISM: Homo sapiens

<400> SEQUENCE: 12

Pro Arg Glu Ala Lys Val Gln Trp Lys Val Asp Asn Ala Leu Gln Ser
 1               5                  10                  15

Gly Asn Ser Gln Glu Ser Val Thr Glu Asn Val Ser Lys Asp Ser Thr
                20                  25                  30

Tyr Ser Leu Ser Ser Thr Leu Thr Leu Ser Lys Ala Asp Tyr Glu Lys
            35                  40                  45

His Lys Val Tyr Ala
        50
```

```
<210> SEQ ID NO 13
<211> LENGTH: 33
<212> TYPE: DNA
<213> ORGANISM: Homo sapiens

<400> SEQUENCE: 13
gtgtcgtgga actcaagcgc tctgaccagc ggc                          33

<210> SEQ ID NO 14
<211> LENGTH: 37
<212> TYPE: DNA
<213> ORGANISM: Homo sapiens

<400> SEQUENCE: 14
gccctccagc agcaacggta cccagaccta catctgc                      37
```

LANDSCAPED ANTIBODIES AND ANTIBODY FRAGMENTS FOR CLINICAL USE

This application claims the benefit of U.S. Provisional application 60/064,386, filed Nov. 6, 1997.

BACKGROUND OF THE INVENTION

1. Field of the Invention

The present invention is directed to glycosylated antibodies and antibody fragments modified to have reactive ketone groups at specific sites. These "landscaped" antibodies and antibody fragments can be conjugated with linkers, peptides, oligosaccharides or other agents useful in clinical applications having a ketone-reactive group, and used to deliver the agents to in vivo target sites.

2. Description of Related Art

Antibody immunoconjugates are widely used in modern medicine. Chemical methods allowing effective conjugation of a variety of diagnostic and therapeutic compounds, including drugs and chelates, to monoclonal antibodies (mabs) are well documented. However, most of these methods rely on random attachments to certain amino acid residues, such as tyrosine, lysine, aspartic acid and glutamic acid. BR-96-DOX 16771 and LL2-*pseudomonas* exotoxin immunoconjugates, which have demonstrated significant anti-tumor activity in tumor-bearing mice, are examples of antibody immunoconjugates constructed through conjugations at these residues. However, because these conjugates are made under extreme chemical conditions (non-physiological pHs, temperature, solvents, etc.) and because the conjugation is not site-specific, the resulting immunoconjugates may exhibit reduced and heterogenous antigen binding properties.

Rodwell et al., *Proc. Nat'l Acad. Sci.*, 83: 2632 (1986), reported site-specific covalent modification of monoclonal antibodies (mAbs) using the Asn-linked carbohydrate (CHO) in the CH2 domain (Asn297) as a convenient chemical handle for radionuclide conjugation. $^{131}$I-conjugates formed by this method exhibited homogenous binding properties with improved in vivo targeting efficiency in mice. By using a soluble amino-dextran as an intermediate carrier, therapeutic drugs, such as methotrexate (MTX), flourouridine, or doxorubicin (DOX), have been conjugated at the CH2-appended carbohydrate moiety. See, for example, U.S. Pat. No. 4,699,784. However, because the Asn297-associated CHO is positioned at the internal space formed between the two adjacent CH2 domains, steric hindrance is expected to impede the efficiency of conjugation at this site. Moreover, antibody fragments, such as F(ab')$_2$, Fab' and Fab, which often are preferred for clinical use, lack the Fc portion and the associated carbohydrate moiety. Accordingly, these species can not be conjugated by this method.

Hansen et al., U.S. Pat. No. 5,443,953, and Leung et al., U.S. Provisional Patent Application 60/013,709, the entire contents of which are incorporated herein by reference, describe the introduction of multiple glycosylation sites on the V$_K$ and CH1 (HCN1 and HCN5 sites) domains of antibodies. Attachment of chelates at all of these sites does not affect the immunoreactivity of the resultant antibody, Leung et al., *J. Immunol.* 154: 5919 (1995), making these carbohydrates ideal site-specific conjugation sites for drugs or chelates. However, in order to conjugate at these carbohydrates, the ribose rings must be chemically oxidized to generate reactive aldehyde groups. Aldehyde groups thus formed can be covalently bonded to the amino groups of chelates or drugs through Schiff bases. Since only the C—C bonds with hydroxyl groups attached to each carbon can be periodate-oxidized to form two aldehyde groups, the maximum number of these reactive sites is dictated by the structure and linkages of the oligosaccharide.

For example, the compositions and sequences of CH1-appended carbohydrates from two antibodies, hLL2HCN1 and hLL2HCN5, have been determined by fluorophore-assisted carbohydrate electrophoresis (FACE) 16411. Qu et al., Glycobiol. 7(6): 803–09 (1997). The structural profile of hLL2HCN1-carbohydrates revealed that about 2–4 hexose rings in an oligosaccharide chain are available for periodate oxidation. Therefore, a maximum of 8–16 aldehyde groups on average can be generated from the carbohydrate side chains of each hLL2HCN1 F(ab')$_2$ fragment. With the average size of hLL2HCN5-carbohydrate being 3–4 monosaccharide residues larger than that of HCN1, a higher number of maximum achievable aldehyde groups for hLL2HCN5 is expected. Under mild chemical conditions, only 1.6 and 3 molecules of DTPA were conjugated to the F(ab')$_2$ of hLL2HCN1 and hLL2HCN5 sites, respectively, probably due to inefficient oxidation of hexose rings under these conditions. Although harsher conditions can be used to generate more aldehyde groups, they may alter the three-dimensional structure of the antibodies and the immunoreactivities of the antibodies may suffer.

Brumeanu et al., *J. Immuno. Meth.* 183: 185–97 (1995), reported coupling peptides to the carbohydrate moieties of antibodies with an enzymatic procedure, in which C-6 aldehydes were generated by oxidizing the terminal galactose (Gal) residues of desialylated immunoglobulins (Igs) with galactose oxidase (GAO). Attachment of peptides is then achieved with concurrent stabilization of the Schiff bases upon mild reduction. The conjugation occurs under physiological conditions, and is specific and efficient with the average number of peptides coupled per Ig being in agreement with the estimated number of galactose equivalents. However, this method requires numerous time consuming steps and cannot be adapted for in vivo conjugation in the context of pretargeting.

There is a need, therefore, for antibodies and antibody fragments that can be conjugated at specific sites to form immunoconjugates useful in clinical applications, such as the diagnosis and treatment of cancer and infectious diseases. There also is a need for a method of making antibody and antibody fragment conjugates wherein the conjugation occurs at specific sites and does not interfere with the specific binding of the antibody or antibody fragment.

SUMMARY OF THE INVENTION

It is, therefore, an object of the present invention to provide antibodies and antibody fragments that can be readily conjugated at specific sites to yield immunoreactive immunoconjugates, and to provide immunoconjugates comprising such antibodies and antibody fragments.

It also is an object of the present invention to provide a method of making antibody and antibody fragment conjugates wherein the conjugation occurs at specific sites and does not interfere with the specific binding of the antibody or antibody fragment.

It also is an object of the present invention to provide methods of targeting an active agent to an in vivo target site using antibodies or antibody fragments that can be readily conjugated at specific sites to yield immunoreactive immunoconjugates, or using immunoconjugates comprising such antibodies or antibody fragments.

In accomplishing these and other objects, one aspect of the present invention provides a method of making a glycosylated antibody or antigen-binding antibody fragment having a reactive ketone group on the glycosylated site, comprising expressing a cell transfected with a vector encoding an antibody having one or more glycosylation sites in a culture medium comprising a ketone derivative of a saccharide or saccharide precursor, and, in the case of an antibody fragment, fragmenting the resulting antibody into an antigen-binding antibody fragment.

In accordance with another embodiment, the present invention provides a method of making an immunoconjugate comprising a glycosylated antibody conjugated to an agent through its glycosylated site, comprising expressing a cell transfected with a vector containing an antibody having one or more glycosylation sites in a culture medium comprising a ketone derivative of a saccharide or saccharide precursor, and reacting the resulting antibody with an agent comprising a ketone-reactive group selected from the group consisting of hydrazides, hydrazines, hydroxylamines, and thiosemicarbazides.

In accordance with another embodiment, the present invention provides a method of making an immunoconjugate comprising a glycosylated antigen-binding antibody fragment conjugated to an agent through the glycosylated site, comprising expressing a cell transfected with a vector containing an antibody having one or more glycosylation sites in a culture medium comprising a ketone derivative of a saccharide or saccharide precursor, fragmenting the resulting antibody into an antigen-binding antibody fragment, and reacting the antibody fragment with an agent comprising a ketone-reactive group selected from the group consisting of hydrazides, hydrazines, hydroxylamines, and thiosemicarbazides.

In accordance with other embodiments, the present invention provides a glycosylated antibody or antigen-binding antibody fragment having a reactive ketone group on the glycosylated site and an immunoconjugate comprising a glycosylated antibody or antigen-binding antibody fragment conjugated to an agent through the glycosylated site.

In accordance with other embodiments, the present invention provides methods of targeting an active agent to an in vivo target site. In accordance with one embodiment, the method comprises administering an immunoconjugate comprising a glycosylated antibody or antigen-binding antibody fragment conjugated to an active agent through the glycosylated site. In accordance with another embodiment, the method comprises administering a glycosylated antibody or antigen-binding antibody fragment having a reactive ketone group on the glycosylation site, and allowing the antibody or antibody fragment to localize at the target site; optionally, administering a clearing agent to clear non-localized antibody or antibody fragment from circulation; and administering an active agent comprising a ketone-reactive group selected from the group consisting of hydrazides, hydrazines, hydroxylamines, and thiosemicarbazides, whereby the active agent localizes at the target site via conjugation with the pre-targeted antibody or antibody fragment.

These and other objects and aspects of the invention will become apparent to the skilled artisan in view of the teachings contained herein.

DETAILED DESCRIPTION OF THE PREFERRED EMBODIMENTS

The present invention provides glycosylated antibodies and antibody fragments landscaped to have reactive ketone groups on the glycosylated sites. By "reactive ketone group" is meant a ketone group reactive with hydrazide, hydrazine, hydroxylamino, and thiosemicarbazide groups under physiological conditions. Such reactive ketone groups are absent in naturally occurring proteins and glycoproteins, and can serve as an efficient molecular handle for the attachment of agents containing a ketone-reactive moiety, such as linkers, peptides, oligosaccharides and other agents useful in clinical applications.

The invention also provides simple and efficient methods of making antibody or antibody fragment immunoconjugates wherein the conjugation occurs through the glycosylated sites and does not interfere with the specific binding of the antibody or antibody fragment. In vivo methods of using the landscaped antibodies and antibody fragments and immunoconjugates also are provided.

Mahal et al., *Science* 276: 1125 (1997), reported that oligosaccharide biosynthetic pathways can be used to substitute cell-surface associated terminal sialic acid residues with sialic acid groups metabolized from N-levulinoyl mannosamine (ManLev), resulting in the formation of a cell surface loaded with reactive ketone residues. Mahal et al. used these cell surface ketones as molecular handles and chemoselectively ligated them to biotinamidocaproyl hydrazides under physiological conditions through the formation of an acyl hydrazone. The biotin-ligated cells were killed when a ricin A chain-avidin conjugate was added.

Mahal et al. indicated that, because transformed cells overexpress a group of antigens often containing both sialic acid and another sugar, fucose, and because some tumor sites have a pH (pH 5) that is more permissible for hydrazide-ketone interactions, the in vivo modification of tumor cells followed by the administration of cytotoxic agents linked to a hydrazide or similar reactive group might be a new modality for treating cancers and other diseases. However, Mahal et al. did not address the possible deleterious effects this method might have on organs landscaped with ketones, and did not address the effects of possible reactions between the ketone-reactive cytotoxic agent and naturally occurring ketone and aldehyde moieties in blood circulation.

The present inventors have discovered that oligosaccharide biosynthetic pathways can be used to introduce reactive ketone groups into N-glycosylation sites on antibodies, and that such landscaped, ketone-containing antibodies (or antigen-binding fragments of these antibodies) can be reacted, either in vitro or in vivo, with ketone-reactive agents to form immunoreactive immunoconjugates.

The landscaped antibodies and antibody fragments of the present invention are made in accordance with the following general procedure: N-linked glycosylation sites are introduced into certain positions of an antibody through genetic engineering. A stable clone expressing the transfected antibody is grown in culture supplemented with a ketone derivative of a saccharide (such as N-levulinoyl fucose) or saccharide precursor (such as N-levulinoyl mannosamine (ManLev)), resulting in an antibody comprising reactive ketone groups at the N-glycosylation sites. In the case of ManLev, biosynthetic pathways convert the ManLev to levulinoyl sialic acid, which is incorporated into the antibody at the glycosylation site. In the case of N-levulinoyl fucose, the N-levulinoyl fucose itself is incorporated into the antibody at the glycosylation site.

Landscaped antigen-binding antibody fragments, including landscaped F(ab), F(ab') and F(ab')$_2$ fragments, are made by fragmenting landscaped antibodies into antigen-binding antibody fragments in accordance with known procedures.

Single-chain antibodies also can be landscaped in accordance with the present invention, for example, using the glycosylation site present in the VK region. In the discussion that follows, it is to be understood that single chain antibodies can be used in place of antibodies.

Although all antibodies are glycoproteins, most of the carbohydrates on the antibodies are N-linked at Asn297 in the CH2 domain. High percentages of the Fc-associated carbohydrates in humans, mice and from hybridomas are incompletely processed, varying in structure-type (complex- or high mannose-type), in the amounts of Sia, Gal and/or GlcNAc residues in the outer branches, and in core fucosylation. Only 12–15% of Fc-associated carbohydrates are sialylated. Landscaping antibodies through naturally occurring Fc-associated carbohydrates therefore is not practical.

Instead, antibodies genetically engineered to have one or more N-glycosylation sites are preferred for landscaping in accordance with the present invention. Such antibodies can be made in accordance with known procedures. U.S. Provisional Patent Application 60/013,709, the contents of which are incorporated herein by reference in their entirety, describes suitable multiply glycosylated antibodies. N-linked glycosylation sites introduced at position 18–20 (VK-N) in the VK domain of an antibody, and at positions 162–164 (HCN1) and 198–200 (HCN5) in the CH1 domain of an antibody, have been shown to be efficiently glycosylated when one site is introduced into an antibody. Similar efficient glycosylation is expected from an antibody engineered to comprise more than one of these sites. Accordingly, antibodies genetically engineered to comprises one or more of these sites are useful in the present invention.

Antibodies hLL2HCN1 and hLL2HCN5 are examples of antibodies engineered to comprise N-glycosylation sites. See co-pending U.S. Pat. No. 5,789,554, the contents of which are incorporated herein in their entirety. The carbohydrates engineered in these antibodies are located on the surface of the CH1 domain and are relatively uniform, all being core-fucosylated, complex-type and heavily sialylated. Antibodies wherein the VH and VK region encoding hLL2is replaced with those of other antibodies of interest also are useful in accordance with the present invention. This replacement can be effected, for example, by simple cut and paste procedures, sequentially using the enzyme pairs Xho1/HindIII and Xba1/BamH1, respectively. A VK region containing a VK-N site can be inserted using a similar approach. See also the examples set forth below.

Antibodies comprising different glycosylation variants can be engineered, such as antibodies engineered with one of the three glycosylation sites described above, or two of them with the combination of VK-N/HCN1: VK-N/HCN5 or HCN1/HCN5, or with all three sites. These sites are advantageous because they can be used in F(ab')$_2$, Fab' or Fab fragments. When IgG is used, the CH2-appended carbohydrate can serve as a fourth possible site for landscaping. Additional glycosylation sites can be identified and engineered in the VK, VH, CH1 CH2, CH3 and CK domains in accordance with procedures known to those skilled in the art.

Growing antibody-producing cells in the presence of a ketone derivative of a saccharide or saccharide precursor efficiently introduces a reactive ketone group onto the N-glycosylation sites through the biosynthetic process. Ketone derivatives of saccharides and saccharide precursors can be used either alone or in combination to introduce ketone groups into the glycosylated antibody. Optionally, the level of antibody production by the clone can be increased by adding methotrexate to the culture.

The concentration of the ketone derivative of the saccharide or saccharide precursor in the cell culture can be controlled to optimize the number of ketone groups introduced into the antibody. The antibody cultures can be grown in any manner, such as roller bottle, fed-batch or continuous flow perfusion bioreactor, as long as the media are supplemented with the ketone derivative of the saccharide or saccharide precursor.

Immunoconjugates comprising these landscaped antibodies or antibody fragments are made by reacting the landscaped antibodies or antibody fragments with an agent containing a ketone-reactive group, such as a hydrazide, hydrazine, hydroxylamino, or thiosemicarbazide group, under physiological conditions. The agent can be, for example, a linker, chelator or diagnostic or therapeutic agent. Any linker, chelator or diagnostic or therapeutic agent can be used, as long as it has a ketone-reactive group. If the landscaped antibody or antibody fragment comprises more than one reactive ketone group, each ketone group can be conjugated to an agent, resulting in an immunoconjugate comprising multiple agent moieties per antibody or antibody fragment.

Examples of agents that can be conjugated to the landscaped antibodies or antibody fragments in accordance with the present invention include linkers, chelators, chelated metals, peptides, oligosaccharides, biotinamidocaproyl hydrazides, diagnostic markers, drugs (for example, methotrexate, flourouridine, and doxorubicin), toxins (such as a ricin A chain), imaging radioisotopes, and therapeutic radioisotopes.

Examples of ligand-containing peptides that can be conjugated to landscaped antibodies in accordance with the present invention include DTPA-bearing peptides, DOTA-bearing peptides, the acyl hydrazides Ac-K$_d$D$_d$K$_d$(TscGC)D$_d$K$_d$-NH(CH$_2$)$_4$CH(NH$_2$)CONH—NH$_2$ and Ac-K$_d$D$_d$K$_d$(TsdGC)D$_d$K$_d$-NH(CH$_2$)$_4$H(NH$_2$)CONH—NH$_2$, and the hydrazine H$_2$N—NH—CH$_2$—CO-D$_d$K$_d$(TscGC)-D$_d$-K$_d$-NH$_2$, where K$_d$ and D$_d$ represent the D-amino acids D-lysine and D-aspartic acid, respectively, and where TscGC is the ligand:

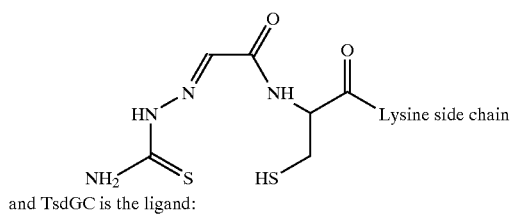

and TsdGC is the ligand:

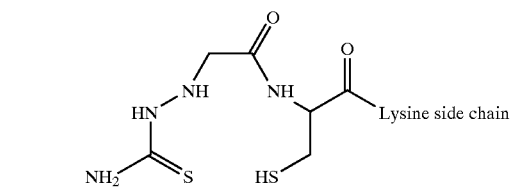

DTPA- and DOTA-containing peptides are suitable for chelating with $^{111}$In and $^{90}$Y; however, extreme conditions such as boiling are required when chelating Tc-99m or Re-188. See, e.g., U.S. Pat. Nos. 5,175,343; 5,120,526 and 5,242,679. These extreme conditions might degrade the conjugated antibody or antibody fragment. In contrast, the acyl hydrazide and hydrazine peptides chelate Tc-99m and Re-188 more readily. For example, the TscGC ligand has been shown to label at room temperature. The ligands of these peptides form stable Tc(V) oxo complexes with the diagnostic imaging isotope Tc99m.

The hydrazine of these peptides is used to form the hydrazone linkage through the ketone to the landscaped antibody or antibody fragment. The hydrophilic amino acids make the peptides sufficiently hydrophilic so that there is no disulfide interchange or mixed disulfide formation during the conjugation of the free thiol containing peptide to the antibody. Surprisingly, the hydrazine peptide forms a more stable antibody conjugate than the acyl hydrazide peptides, with the acyl hydrazide peptide-antibody conjugates exhibiting loss of labeled peptide after 24 hours. See the discussion in Example 8 below.

The D amino acids of the peptides minimize metabolism of the metal complexed peptide after injection. Accordingly, in the event that the protein is degraded, the hydrophilic metal-containing peptide will not be metabolized. Moreover, because it is hydrophilic, any labeled peptide which escapes the cell will be rapidly excreted renally.

Antigenic epitopes also can be conjugated to the landscaped antibodies or antibody fragments. For example, oligosaccharides containing the α-Gal epitope covalently linked to a hydrazide group via —$(CH_2)_n$— linkers can be used. Tumor-specific antibodies or antibody fragments conjugated with such epitopes elicit immune responses via natural anti-Gal antibodies. See U.S. Provisional Patent Application 60/037,908, the contents of which are incorporated herein by reference in their entirety.

Landscaped antibodies can be harvested and conjugated in at least three different ways:

1. At the end of culture, antibodies are purified by standard protein A affinity column procedures. The purified antibodies landscaped with ketones are mixed with an agent comprising a ketone-reactive group, such as a hydrazide or hydrazine group. The rapid hydrazide-ketone reaction results in the formation of antibody conjugates covalently linked via the acyl-hydrazone at the engineered carbohydrate in a site-specific manner.

2. At the end of culture, the media are overloaded with agents containing ketone-reactive groups. The excess hydrazides neutralize any unincorporated sugar, landscaped cellular glycoproteins or glycolipids, and are conjugated with the landscaped antibodies. The acidic environment resulting from terminal cultures encourages reactions between, for example, hydrazides and ketones, which occurs 10 times faster at pH 5 than at pH 7.3–7.6). The conjugated antibodies are purified using protein A columns.

3. At the end of culture, landscaped antibodies are bound to protein A and reacted directly with the agents before the antibodies are washed and eluted from the column. This procedure avoids the loss of some reactive ketone sites which may occur in the protein A column.

The following reaction scheme illustrates the reaction between a hydrazide-containing molecule and a ketone-landscaped antibody or antibody fragment:

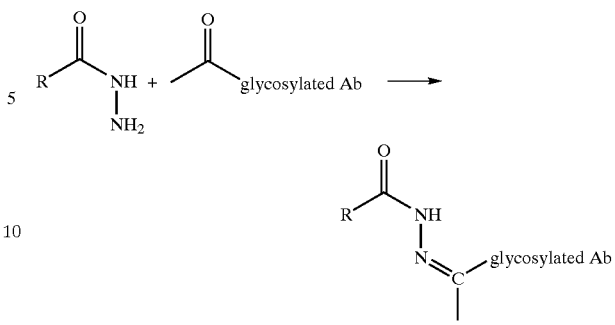

where R represents the hydrazide-containing agent, and glycosylated Ab represents the glycosylated antibody or antibody fragment.

In accordance with one embodiment of the invention, the ketone-reactive group comprises a hydrazide derivative of aspartic acid. The following reaction scheme illustrates the reaction between this type of agent and a ketone-landscaped antibody or antibody fragment:

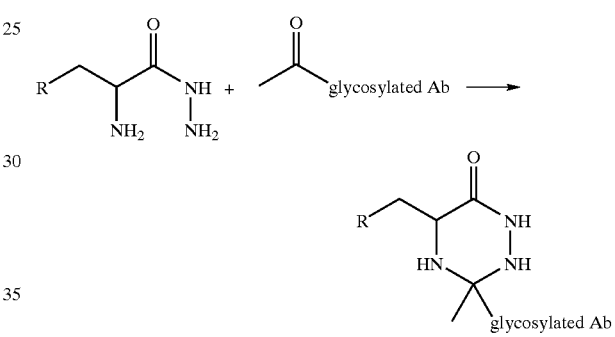

R represents the hydrazide-containing agent, and glycosylated Ab represents the glycosylated antibody or antibody fragment. The reaction will occur under the same conditions as other acyl hydrazide-ketone reactions. For example, a pH of about 5 is advantageous, but the reaction will proceed at a pH of up to about 7.3–7.6. This reaction will occur rapidly, and the resulting conjugate may be stable without a separate stabilization step, such as a sodium cyanoborohydride reduction.

Antibodies and antibody fragments specific for tumors, pathogens, and other molecules of clinical interest can be landscaped in accordance with the present invention and used in clinical applications, such as the diagnosis and treatment of cancer or other pathologies, including viral, bacterial and parasitic infections. The landscaped antibodies can be directly conjugated to a diagnostic or therapeutic agent comprising a ketone-reactive group, or can be conjugated to a diagnostic or therapeutic agent through a chelator which comprises a ketone-reactive group. The resulting immunoconjugate can be administered in vivo in accordance with standard immunodiagnostic or immunotherapeutic procedures to effect diagnosis or treatment of the cancerous or other pathological condition.

Alternatively, landscaped antibodies or antibody fragments specific for tumors, pathogens, and other molecules of clinical interest can be used in pretargeting methods. In one example of a pretargeting method in accordance with the present invention, the landscaped antibody or antibody fragment is administered and allowed to localize at a target site, such as a tumor or lesion. Then, the diagnostic or therapeutic agent comprising a ketone-reactive group (or a diagnostic or therapeutic agent chelated by a chelating agent comprising a ketone-reactive group) is administered. This agent reacts with the localized landscaped antibody or antibody fragment, thereby delivering diagnostic or therapeutic agent to the target site. Although the ketone-reactive agent also may react with circulating molecules that contain ketone groups, any such reactions are not expected to produce problematic adverse effects because these molecules are not cell-surface bound, as they were in the method of Mahal et al.

In accordance with another pretargeting method of the present invention, a clearing agent is administered after the landscaped antibody has localized at the target site (and before the diagnostic or therapeutic agent is administered) in order to clear non-localized antibody from circulation. Advantageously, the clearing agent is anti-idiotypic to the landscaped antibody, such as an anti-idiotypic antibody. U.S. patent application Ser. No. 08/486,166 and U.S. Pat. No. 5,965,131, the contents of which are incorporated by reference herein in their entirety, describe anti-idiotypic clearing agents useful in accordance with the present invention.

The embodiments of the invention are further illustrated through the following examples which show aspects of the invention in detail. These examples illustrate specific aspects of the invention and do not limit its scope.

EXAMPLE 1

Re-engineering of a Naturally Occurring N-linked Carbohydrate in Humanized Antibodies A potential Asn-linked glycosylation site at the Vκ FRI region was identified in the anti-B-cell monoclonal antibody denoted LL2. This site was confirmed to be used for glycosylation, and the attached CHO, as predicted by computer modeling studies, was positioned away from the antigen binding site (ABS). The conjugation of chelates, DTPA, or DTPA derivatives onto this V-appended CHO was not observed to have any adverse effects on the immunoreactivity of the resultant conjugates, whereas random conjugation of a comparable number of chelates to lysine residues resulted in a substantial reduction in immunoreactivity. See Table 1 below. The ability of this V-appended CHO to serve as a universal conjugation site, especially for antibody fragments devoid of the Fc domains, was demonstrated when the LL2 glycosylation site was grafted onto the corresponding region in the V domain of hMN14, and the grafted site in the re-engineered mAb was shown to be glycosylated. Neither glycosylation at this site nor chelate attachment on the engineered CHO was observed to affect the resultant immunoreactivities of the mAb. All CHO conjugates studied were efficiently labeled with $^{111}$In or $^{90}$Y.

TABLE 1

Conjugation chemistry and radiolabeling of Ab F(ab')$_2$

| | mLL2F(ab')$_2$ | | | hMN14F(ab')$_2$ | |
|---|---|---|---|---|---|
| Conjugation Site | Vκ-CHO | | Random Lysin | Nil | Vκ-CHHO |
| Chelators | DTPA | LC-DTPA | DTPA | DTPA | LC-DTPA |
| No. of chelators/F(ab')$_2$ | 5.5 | 4.6 | 2.2 | 4.3 | 0.075 | 2.1 |
| Immunoreactivity[a] | 100 | 100 | 75 | 21 | ND | 100 |
| %$^{111}$In labeling | 89.4 | 86.6 | | | | 91.6 |
| (μCi/μg) | (7.5) | (12.7) | | | | (1.3) |
| %$^{90}$Y labeling | 85.3 | 87.4 | ND | ND | ND | ND |
| (μCi/μg) | (4.3) | (1.6) | | | | |

[a]On the bases of comparisons to the ID$_{50}$ of unmodified control F(ab')$_2$ in competitive binding assay.

EXAMPLE 2

Designing and Engineering N-linked CHOs in the CH1 Domain of hLL2

To engineer novel CHO moieties, the glycosylation acceptor sequences, Asn-X-Ser/Thr, were introduced into the Cκ and CH1 domains of hLL2 by site-specific mutagenesis. Although the tripeptide sequence is necessary for directing the N-linked glycosylation in proteins, efficient glycosylation only occurs at the properly positioned acceptor. Sites were designed that are: (1) naturally found in the constant domains of other antibodies, (2) at a surface position as identified by computer modeling, or (3) randomly selected sites "evenly" dispersed along the Cκ and CH1 domains, in order to identify proper positions for efficient glycosylation. A total of five CH1 sites (HCN1-5) and five Cκ sites (KCN1-5) were designed and engineered.

Table 2 shows the positions and sequences of N-glycan acceptors in the CH1 and Cκ domains of hLL2. Site-directed mutagenesis was used to generate the tri-peptide acceptor sequences (bold letters). Partial peptide sequences of the CH1 (H chain) and Cκ (L chain) domains of hLL2 are shown and aligned according to sequence and structure homology to indicate the positional relationship between the engineered potential Asn-linked glycosylation sites (HCN1-HCN5 and KVN1-KCN5). The β-strand sequences (C-F) are boxed. The residues were numbered according to Kabat's system; the heavy chain residues that were numbered discontinuously from the previous ones are indicated with asterisk (*) and these residues from left to right are numbered as 156, 162, 171, 182, 203, and 205, respectively.

TABLE 2

| | 149 | * * | * | * | **207 | | |
|---|---|---|---|---|---|---|---|
| H chain | PEPVTVSWNSGALT---SGVHTFPAVLQSSGLYSLSSVVTV-PSSSLGTQTYI | | | | | (SEQ ID NO:1) |
| HCN1 | PEPVTVSWNSSALT---SGVHTFPAVLQSSGLYSLSSVVTV-PSSSLGTQTYI | | | | | (SEQ ID NO:2) |
| HCN2 | PEPVTVSWNSGALT---SGVHTFPAVLNSSGLYSLSSVVTV-PSSSLGTQTYI | | | | | (SEQ ID NO:3) |
| HCN3 | PEPVTVSWNSGALT---SGVHTFPAVLQSSGLYSNSSVVTV-PSSSLGTQTYI | | | | | (SEQ ID NO:4) |
| HCN4 | PEPVTVSWNSGALT---SGVHTFPAVLQSSGLYSLSSVVTV-PNSSLGTQTYI | | | | | (SEQ ID NO:5) |
| HCN5 | PEPVTVSWNSGALT---SGVHTFPAVLQSSGLYSLSSVVTV-PSSSNGTQTYI | | | | | (SEQ ID NO:6) |
| | 141 | | | 193 | | | |
| K chain | PREAKVQWKVDNALQSGNSQESVTEQDSKDSTYSLSSTLTLSKADYEKHKVYA | | | | | (SEQ ID NO:7) |
| KCN1 | PREAKVQWKVDNALQSGNSNESVTEQDSKDSTYSLSSTLTLSKADYEKHKVYA | | | | | (SEQ ID NO:8) |
| KCN2 | PREAKVQWKVDNALQSGNSQESVTEQDSKDSTYNLSSTLTLSKADYEKHKVYA | | | | | (SEQ ID NO:9) |
| KCN3 | PREAKVQWKVDNASQSGNSQESVTEQDSKDSTYSLSSTLTLSKADYEKHKVYA | | | | | (SEQ ID NO:10) |
| KCN4 | PREAKVQWKVDNALQSGNSQESVTEQDSKDSTYSLSSTLNLSKADYEKHKVYA | | | | | (SEQ ID NO:11) |
| KCN5 | PREAKVQWKVDNALQSGNSQESVTENVSKDSTYSLSSTLTLSKADYEKHKVYA | | | | | (SEQ ID NO:12) |
| β-strand | C | D | E | F | | | |

In all cases except for KCN5, possible perturbations in the final tertiary structure were minimized by carefully choosing sequences that required only single amino acid substitution to become a potential glycosylation site. In the case of KCN5, two amino acid residues were changed to form the sequence Asn-Val-Ser (166–168). None of these sites appeared to be "buried" or at the interface between two juxtaposed domains, as evaluated by computer modeling analyses.

To examine whether these engineered sites were efficiently glycosylated, the antibody mutants were purified from stably transfected cells and analyzed in SDS-PAGE under reducing conditions. The heavy chains of the mutant antibodies hLL2HCN1-5 migrated at slower rates, due to glycosylation at the engineered sites, compared to that of the parent antibody, hLL2, whose CH1 domain did not contain any potential glycosylation sites. From the relative migration rates of the peptides in SDS-PAGE, which are inversely proportional to the molecular sizes, the extent of glycosylation at the different sites was estimated to be HCN5>HCN1>HCN3>HCN2>HCN4, with hLL2HCN5 and hLL2HCN1 being the two most highly glycosylated antibodies. In contrast, the lack of migration retardation in the light chains for the mutants hLL2KCN1-5, led to the conclusion that these Cκ-associated sites were not glycosylated.

Because all human IgGs are naturally glycosylated in the CH2 domain at Asn297, there was a possibility that the size differences between the mutant antibodies and hLL2 observed in SDS PAGE might be due to differential glycosylation at Asn297, rather than at the engineered sites, as a result of variations in the culture condition. When the F(ab')$_2$ fragments of hLL2HCN1, hLL2HCN5 and hLL2 were prepared for SDS-PAGE analyses, it was confirmed that the size differences between the antibodies were indeed associated with the Fd fragments (VH-CH1), which are devoid of the Fc portion and the appended oligosaccharides. Accordingly, the size differences between the mutant antibodies and hLL2 observed in SDS PAGE were not due to differential glycosylation at Asn297.

To quantitatively evaluate the sizes of these CH1-appended oligosaccharides, F(ab')$_2$ fragments of hLL2, hLL2HCN1 (glycosylation site at Asn 162; tripeptide acceptor NGS) and hLL2HCN5 (glycosylation site at Asn 198; tripeptide acceptor NGT) were prepared and subjected to mass spectrometry analysis (Mass consortium, San Diego, Calif.). The mass spectrometry-measured molecular mass of the F(ab')$_2$ fragments of hLL2, hLL2HCN1 and hLL2HCN5 were 99,471, 102,884 and 104,345, respectively. Since the Fc portion containing the CH2-appended CHO was excluded, the mass difference between the F(ab')$_2$ fragments of non-glycosylated hLL2 and the glycosylation mutants should represent the mass of the engineered, CH1-appended CHOs. Therefore, the molecular sizes of HCN1- and HCN5-appended CHOs were calculated to be approximately 3,400 and 4,900 daltons, respectively. Taking the molecular weight of an average monosaccharide residue to be 240, we estimated that HCN5-appended CHO contained three to four more monosaccharide residues than attached to the HCN1 site. This was confirmed by detailed structural analysis of the engineered CHOs.

EXAMPLE 3

Structure Determination of CHOs Associated with HCN1 and HCN5 sites

The structures of HCN1- and HCN5-appended CHOs were determined using FACE, which involves releasing, separating, quantifying and sequencing complex oligosaccharides from glycoproteins. N-linked oligosaccharides were released from hLL2HCN1 or hLL2HCN5 by PNGase F digestion, purified, and then labeled with fluorophore 8-aminonaphthalene-1,3,6-trisulfonic acid (ANTS) at the free reducing end. Because one molecule of ANTS attaches to one molecule of oligosaccharide, the relative amount of different CHO species can be accurately determined after fractionation in high concentration polyacrylamide gel. Qu et al., Glycobiol. 7(6): 803–09 (1997).

Heterogeneous populations of oligosaccharides were released from the F(ab')$_2$ fragments of hLL2HCN1 and hLL2HCN5. The profile of HCN5 oligosaccharides was very different from that of HCN1. For example, while N1-b was the most abundant species, accounting for 55% of all labeled oligosaccharides from the HCN1 site, N5-b1, which was structurally identical to N1-b, accounted for less than 20% of the labeled HCN5 oligosaccharides.

To examine and compare structural similarities and differences between HCN1- and HCN5-appended CHOs, we sequenced the individual ANTS-labeled species and elucidated the topological structures. All HCN1- and HCN5-CHO species sequenced were found to be core-fucosylated, complex-type, and all branches were fully elongated, containing Gal and GlcNAc residues. This is in accordance with our goal that the sites (HCN1 and HCN5) should be at exposed positions on the antibody.

Both the HCN1 and HCN5 sites are efficiently utilized for glycosylation. The CHOs on HCN1 are predominantly biantennary (100%) and the CHO on HCN5 is mostly triantennary (60%). Significantly, as much as 60 and 90% of the HCN1- and HCN2-CHOs were sialylated, respectively. Of those that were sialylated, Sia residues could be identified in all the outer branches of either biantennary or triantennary structures. Therefore, these engineered CHOs provide abundant potential sites for antibody landscaping. Additionally, the fact that all HCN1- and HCN5-CHO species contain a fucose residue attached to the pentasaccharide core indicates that a ketone handle can be introduced site-specifically on the surface of IgG by biosynthetically incorporating N-levulinoyl fucose (FucLev) into the engineered CHOs.

EXAMPLE 4

Generation of Antibodies Carrying Multiple Glycosylation Sites

Using the PCR method described in Leung et al., *J. Immunol.* 154: 5919 (1995), the Vκ-N (NVT) glycosylation site is introduced to the Vκ-domain of an antibody with a known DNA sequence. The engineering of both the HCN1 (NSS) and HCN5 (NGT) sites into a single CH1 domain is effected by site-directed mutagenesis using the Sculptor IVM system (Amersham, Arlington Heights, Ill.). Briefly, the segment of genomic DNA encoding the human IgG1 [CH1 intron-hinge-intron-CH2-intron-CH3] is spliced out from the heavy chain expression vector hLL2pdHL, Losman et al., *Cancer Supp.* (1997), in press. Using the enzyme pair Hind111/Eag1. The 2 kb fragment is then ligated into the corresponding cloning sites of pBlueScript SK vector (Strategene, La Jolla, Calif.). The oligonucleotide HCN1 (5'-GTG TCG TGG AAC TCA AGC GCT CTG ACC AGC GGC-3') (SEQ ID NO:13) is used to introduce a G164S (numbered according to Kabat's numbering) substitution in the CH1 domain. Successful mutation is confirmed by DNA sequencing. Using the heavy chain fragment containing the HCN1 mutation in CH1 as the template, a second mutation is introduced using the oligonucleotide HCN5 (5'-G CCC TCC AGC AGC AAC GGT ACC CAG ACC TAC ATC TGC-3') (SEQ ID NO:14) for a L198N substitution. The presence of both the HCN1 and HCN5 sites in the predetermined position is confirmed by DNA sequencing. The HindIII/EagI fragment containing the mutated human IgG1 heavy chain genomic sequence is ligated back to the corresponding position of hLL2pdHL2. The resultant vector is designated as hLL2pdHL2(HCN1/5).

EXAMPLE 5

Landscaping Glycosylated Antibodies

Expression vector hLL2pdHL2(HCN1/5) is transfected into SP2/0 cells using standard procedures. See, e.g., Leung et al., *Int. J. Cancer* 60: 534 (1995). Clones producing transfected antibodies are identified by ELISA assay. The levels of antibody production by these clones are enhanced by amplification with increasing concentrations of methotrexate in culture. See Leung et al., *Tumor Target.* 2: 184(96) (1996); Losman et al. *Tumor Target.* 2: 155(41) (1996).

A stable clone expressing high levels of antibody is grown in culture supplemented with about 5 mM of ManLev. The biosynthetic pathway results in the formation of reactive ketone groups on the glycosylated sites.

EXAMPLE 6

Conjugation of Landscaped Antibodies to Chelating Agents

The glycosylated mutant antibodies, hLL2HCN1 and hLL2HCN5, exhibited identical binding affinity for WN in an ELISA assay, as compared to that of the parent antibody. Under mild chemical conditions specific for CHO conjugation, an average of 1.6 and 2.97 molecules of DTPA were incorporated in each $F(ab')_2$ fragment of hLL2HCN1 and hLL2HCN5, respectively. Both conjugates demonstrated high efficiencies in $^{111}$In incorporation (92% for hLL2HCN1, 91% for hLL2HCN5). No significant changes in immunoreactivities were observed before and after DTPA conjugation of the glycosylation mutant fragments. The HCN5-appended CHO appeared to be more accessible for chelate conjugation when compared to the HCN1 appended CHO, with almost twice as many DTPA molecules incorporated into the HCN5 site. This is consistent with the finding that the CHOs attached at the HCN5 site were larger than that at the HCN1 site.

TABLE 3

| Antibody | | Efficiency | $^{111}$In labeling | | Immunoreactivity[a] | |
|---|---|---|---|---|---|---|
| $F(ab')_2$ | DTPA | $DTPA/F(ab')_2$ | % Incorp. | μCi/μg | $ID_{50}$μg/ml | % of hLL2 |
| hLL2 | Non-conjugated | NA | NA | NA | 0.384 + 0.021 | 100 |
| hLL2HXN1 | Non-conjugated | NA | NA | NA | 0.355 + 0.038 | 92.4 |
| | Conjugated | 1.6 | 92 | 6 | 0.387 + 0.042 | 100.8 |
| hLL2HCN5 | Non-conjugated | NA | NA | NA | 0.443 + 0.039 | 115.4 |
| | Conjugated | 2.97 | 91 | 5.6 | 0.356 + 0.077 | 92.7 |

[a]On the basis of comparisons to the $ID_{50}$ of unmodified hLL2 $F(ab')_2$ in competitive binding assays.
NA: not available

EXAMPLE 7

Conjugation of Landscaped Antibodies to Large Drug Molecules

The effect of site-specific attachment of large drug complexes, DOX-dextran, to antibodies through the landscaped ketone groups also was studied. The DOX-dextran complex was generated by chemically incorporating an average of 10 DOX molecules onto an 18 kDa amino-dextran polymer.

In contrast to most V region-associated CHOs, whose physical proximity to the antibody binding site would alter the immunoreactivity as a result of their removal or modification, computer modeling studies indicate that the naturally occurring CHO in the Vκ, domain of murine LL2 is positioned remotely from the antibody binding site. This is consistent with the fact that the antigen-binding affinity of LL2 was not tempered when its Vκ-appended CHO was moderately modified and conjugated with small chelates, such as DTPA. However, using the amino-dextran as a carrier for DOX, an incorporation ratio of 5.1 DOX molecules per $F(ab')_2$ of LL2 resulted in a reduction of close to 60% of immunoreactivity, as evaluated by cell binding and ELISA assays, revealing that the so-called remote CHOs are too close to the antibody binding site for conjugation with large drug complexes.

The engineered CHOs in hLL2HCN1 and hLL2HCN5 have the advantages of being farther away from the antibody binding site, and importantly, are in a separate globular structure ($CH_1$ domain) from V regions. Therefore, these CHOs exhibit less interference with the antibody binding site, and, therefore, less reduction in immunoreactivity, when they are conjugated to large compounds. Conjugation of DOX-dextran complexes to the $F(ab')_2$ of hLL2HCN1 under identical conditions resulted in a DOX-incorporation ratio of 6.8, with comparatively less detrimental effect (30% reduction) in the resultant binding affinity. When a similar number of DOX molecules (7.1) was conjugated to the $F(ab')_2$ of hLL2HCN5, the resultant immunocomplex retained 95% of the antigen binding affinity. These results demonstrated the spatial relationship between the engineered CHOs and the antibody binding sites and were consistent with the computer models, which show that the HCN1-CHO is anchored in the mid section of the C β-strand and is tilted toward the antibody binding site, whereas the HCN5-CHO is positioned in the tip at the bottom loop of the β-barrel forming the CH1 domain, and is pointed at an angle away from the antibody binding site.

TABLE 4

| Antibody $F(ab')_2$ | DOX-dextran | Efficiency[D] $(DOX/F(ab')_2)$ | Immunoreactivity (%) Cell binding[c] | ELISA[d] |
|---|---|---|---|---|
| LL2[a] | Non-conjugated | NA | 100 | 100 |
| | conjugated | 5.1 | 41.9 | 42.2 |
| hLL2HCN1 | Non-conjugated | NA | 100 | 100 |
| | conjugated | 6.8 | 70 | 70.6 |
| hLL2HCN5 | Non-conjugated | NA | ND | 100 |
| | conjugated | 7.2 | ND | 94.8 |

[a]Murine mAb, naturally glycosylated in the V domain.
[b]Determined and calculated by absorbance at 482 nm for the drug concentration (_ = 154 for 1% DOX in PBS) and by the dry weight of dextran {270}.
[calculated] from the $ID_{50}$ values.
[d]The immunoreactivity calculated from the $ID_{50}$ values of the competitive binding assay with WN as the surrogate Ag.
NA: not available.
ND: not determined.

EXAMPLE 8

Bifunctional Peptide Comprising Landscaped Antibody or Antibody Fragment

A bifunctional peptide, IMP-155, was designed which contains a glycylhydrazine linker for linkage to an antibody or antibody fragment, and a metal binding ligand group. The peptide also comprises several hydrophilic D amino acids. IMP-155 and several analogues were synthesized by standard Fmoc-based peptide synthesis on an Advanced Chemtech 348 multiple peptide synthesizer. The molecular weight of purified IMP-155 was determined by mass spectrometry (ESMS) to be $MH^+$ 808, which was identical with the calculated value.

In preliminary conjugation experiments, we compared the conjugation and stability of acyl hydrazide linkers with glycylhydrazine linkers and found that the acyl hydrazides were unstable. After incubation of the purified acyl hydrazide conjugates in pH 7.3 buffer at room temperature for 24 hr, about 20–40% of the attached peptides were released from the antibody. In contrast, the glycylhydrazine linker showed little (<3%) decomposition under the same storage conditions. Therefore, the glycylhydrazine was chosen as the linker for the synthesis of IMP-155.

The structure of IMP-155 is $H_2N—NH—CH_2—CO\text{-}D_d\text{-}K_d\text{-}(TscGC)\text{-}D_d\text{-}K_d—NH_2$, where $K_d$ and $D_d$ represent the D-amino acids D-lysine and D-aspartic acid, respectively, and TscGC is:

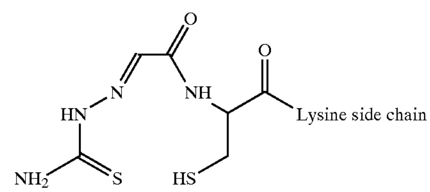

IMP-155 is conjugated to a purified landscaped antibody or antibody fragment in a molar ratio of 1:100 peptide:antibody at pH 5.3 in acetate buffered saline for 2 hours at room temperature. The conjugated antibody or antibody fragment is purified twice through sephadex G 50–80 gel spin columns to remove unbound excess peptide.

EXAMPLE 9

Direct Targeting with Landscaped Antibodies Conjugated to Active Agents

Landscaped antibodies or antibody fragments specific for a tumor, pathogen or other site of clinical interests (collectively referred to as "the target site") are conjugated in vitro to an active agent, such as a diagnostic or therapeutic agent, comprising a ketone-reactive group. The resulting conjugate is injected into a patient and localizes at the target site via specific binding by the antibody or antibody fragment.

EXAMPLE 10

Pretargeting with Landscaped Antibodies Carrying Reactive Ketone Groups

Landscaped antibodies or antibody fragments specific for a target site are directly injected into a patient. After the antibodies are targeted to the target site and, optionally, after unbound antibodies have been cleared from circulation with a clearing agent, an active agent (e.g., a diagnostic or therapeutic agent) containing a ketone-reactive group is administered. This active agent reacts with the target-bound-landscaped antibodies, thereby delivering active agent to the target site.

It will be apparent to those skilled in the art that various modifications and variations can be made to the processes and compositions of this invention. Thus, it is intended that the present invention cover the modifications and variations of this invention provided they come within the scope of the claims and their equivalents.

What is claimed is:

1. A method of making a glycosylated antibody having a reactive ketone group on the glycosylated site, comprising:

expressing SP2/0 cells that are transfected with a vector encoding an antibody having one or more N-glycosylation sites in the CH1 or Vκ domain in a culture medium comprising a ketone derivative of a saccharide or biosynthetic saccharide precursor, where the ketone derivative of the saccharide or biosynthetic saccharide precursor is selected from the group consisting of N-levulinoyl mannosamine and N-levulinoyl fucose, so that they produce a glycosylated antibody having a reactive ketone group on the glycosylated site.

2. The method of claim 1, wherein the antibody has more than one glycosylation site.

3. The method of claim 1, wherein the antibody is a single-chain antibody.

4. A method of making a glycosylated antigen-binding antibody fragment having a reactive ketone group on the glycosylated site comprising:

expressing SP2/0 cells that are transfected with a vector encoding an antibody having one or more N-glycosylation sites in the CH1 or Vκ domain in a culture medium comprising a ketone derivative of a saccharide or biosynthetic saccharide precursor, wherein said ketone derivative of the saccharide or biosynthetic saccharide precursor is selected from the group consisting of N-levulinoyl mannosamine and N-levulinoyl fucose, so that they produce a glycosylated antibody having a reactive ketone group on the glycosylated site, and fragmenting the resulting glycosylated antibody to produce a glycosylated antigen-binding antibody fragment having a reactive ketone group on the glycosylated site.

5. The method of claim 4, wherein the fragment is an F(ab')$_2$ fragment.

6. A method of making a glycosylated antibody having a reactive ketone group on the glycosylated site, comprising:

expressing SP2/0 cells that are transfected with a vector encoding an antibody having a HCN1, HCN5 or Vκ N-glycosylation site in a culture medium comprising a ketone derivative of a saccharide or biosynthetic saccharide precursor, where the ketone derivative of the saccharide or biosynthetic saccharide precursor is selected from the group consisting of N-levulinoyl mannosamine and N-levulinoyl fucose, so that they produce an N-glycosylated antibody having a reactive ketone group on the glycosylated site.

7. A method making a glycosylated antigen-binding antibody fragment having a reactive ketone group on the glycosylated site, comprising:

expressing SP2/0 cells that are transfected with a vector encoding an antibody having a HCN1, HCN5 or Vκ N-glycosylation site in a culture medium compnsing a ketone derivative of a saccharide or biosynthetic saccharide precursor, where the ketone derivative of the saccharide or biosynthetic saccharide precursor is selected from the group consisting of N-levulinoyl mannosamine and N-levulinoyl fucose, so that they produce a glycosylated antibody having a reactive ketone group on the glycosylated site, and fragmenting the resulting glycosylated antibody into a glycosylated antigen-binding antibody fragment having a reactive ketone group on the glycosylated site.

* * * * *